(12) United States Patent
Santaniello et al.

(10) Patent No.: US 6,255,503 B1
(45) Date of Patent: Jul. 3, 2001

(54) WATER-SOLUBLE SALTS OF DODECANDIOIC ACID AND PHARMACEUTICAL AND NUTRITIONAL COMPOSITIONS CONTAINING SAME

(75) Inventors: Mosé Santaniello, Nettuno; Nazareno Scafetta, Pavona di Albano; Maria Ornella Tinti, Rome, all of (IT)

(73) Assignee: Sigma-Tau Healthscience S.p.A., Rome (IT)

( * ) Notice: Subject to any disclaimer, the term of this patent is extended or adjusted under 35 U.S.C. 154(b) by 0 days.

(21) Appl. No.: 09/424,252

(22) PCT Filed: May 29, 1998

(86) PCT No.: PCT/IT98/00144

§ 371 Date: Nov. 30, 1999

§ 102(e) Date: Nov. 30, 1999

(87) PCT Pub. No.: WO98/54119

PCT Pub. Date: Dec. 3, 1998

(30) Foreign Application Priority Data

May 30, 1997 (IT) .............................. RM97A0322

(51) Int. Cl.$^7$ .................................................. C07C 101/00
(52) U.S. Cl. ........................ 554/104; 554/121; 562/553; 562/562; 562/561
(58) Field of Search ............................ 554/104; 562/553, 562/562, 561

(56) References Cited

FOREIGN PATENT DOCUMENTS

| 733119 | * 4/1966 | (CA) . |
|---|---|---|
| 0 000 158 | 1/1979 | (EP) . |
| 2 235 938 | 1/1975 | (FR) . |
| 2 048 262 | 12/1980 | (GB) . |
| 48 043 487 | 6/1973 | (JP) . |
| WO 92 12960 | 8/1992 | (WO) . |

* cited by examiner

Primary Examiner—Deborah D. Carr
(74) Attorney, Agent, or Firm—Oblon, Spivak, McClelland, Maier & Neustadt, P.C.

(57) ABSTRACT

Water-soluble dodecandioates wherein the cationic moiety is selected from the group comprising the cations of basic aminoacids (e.g. lysine) and choline and orally or parenterally administrable compositions containing same, are disclosed.

11 Claims, No Drawings

WATER-SOLUBLE SALTS OF DODECANDIOIC ACID AND PHARMACEUTICAL AND NUTRITIONAL COMPOSITIONS CONTAINING SAME

This application is a 371 of PCT/IT98/00144 filed May 29, 1998.

BACKGROUND OF THE INVENTION

1. Field of the Invention

The present invention relates to water-soluble salts of dodecandioic acid and compositions with therapeutic or nutritional activity containing such salts.

Dodecandioic acid, $HOOC(CH_3)_{10}COOH$, and its derivatives such as amides with amino acids, triglycerides and their pharmacologically acceptable salts have recently aroused substantial interest in the nutritional field.

2. Description of the Related Art

EP 0569393 B1 discloses the use of linear C6–C12 dicarboxylic acids, including dodecandioic acid, and their esters, amides and triglycerides in enteral and parenteral nutrition in which the use of such dicarboxylic acids with an even number of carbon atoms as an alternative energy substrate proves particularly useful in those conditions wherein the utilisation of glucose and/or free fatty acids is prevented.

Since these linear acids with an even number of carbon atoms are symmetrical, they can be β-oxidised starting from the α or ω-carboxyl group supplying acetyl CoA and succinic acid as the end product The increased availability of succinic acid stimulates the metabolism of other substrates via the Krebs cycle. In addition, succinic acid is a gluconeogenic precursor, with the result that the administration of such acids is believed to increase the accumulation of glycogen in those clinical conditions that give rise to a decrease in glycogen owing to inadequate glycogen-synthase activity (as occurs in diabetes mellitus) and to reduce the catabolic breakdown of amino acids in conditions of increased glycogenolysis (as occurs in conditions of sepsis, trauma or major abdominal surgery).

Dodecandioic acid has also recently been proposed for cosmetic use, particularly for the production of creams for the treatment of wrinkles, for the regeneration of the skin and to combat the damage of ageing and exposure to the sun's rays.

BRIEF SUMMARY OF THE INVENTION

All the above-mentioned applications are facilitated when derivatives of dodecandioic acid are available which are water-soluble, since dodecandioic acid is known to be practically insoluble in water (0.05 g in 1 liter of $H_2O$ at 23° C.; Ber. 23, 2347 [18901]). Water-soluble derivatives of dodecandioic acid could, on the other hand, be easily administered and promptly used as an energy substrate.

Water-soluble salts of dodecandioic acid are already known.

Such salts are, however, dodecandioates of alkaline metals, particularly sodium. The administration of substantial amounts of these salts, particularly by parenteral nutrition, may alter the electrolyte balance in subjects who are already severely debilitated by the disease or surgical intervention that makes parenteral nutrition necessary and may prove damaging in general in anyone obliged to go on a low-sodium diet.

One object of the present invention is to provide water-soluble salts of dodecandioic acid which do not present the aforesaid drawbacks.

A further object of the present invention is to provide water-soluble salts of dodecandioic acid, whose cationic moiety, unlike the above-mentioned known salts, presents an intrinsic therapeutic or nutritional value.

It should, therefore, be clearly understood that the usefulness of the salts of the present invention does not consist merely in their water-solubility but also in the fact that such salts present as a whole an increased therapeutic and/or nutritional value as compared to the known dodecandioates, this latter value therefore not being exclusively brought about by the anionic moiety of the salt.

DETAILED DESCRIPTION OF THE INVENTION

In accordance with the present invention, the aforesaid objects are achieved by the dodecandioic acid salts of general formula (I):

$$[^-OOC(CH_2)_{10}COO^-]X^+Y^+ \qquad (I)$$

wherein:

if $X^+$ is the same as $Y^+$, it is selected from the group comprising the cations of basic amino acids and choline; or if $X^+$ is other than $Y^+$, they are selected from:
(a) the cations of basic aminoacids and choline; and
(b) the cations of alkaline metals and ammonium, provided that if either of $X^+$ or $Y^+$ is a (b) cation, the other is an (a) cation.

The cations of the basic aminoacids are the cations of lysine, arginine, hystidine and ornithine, while the cations of the alkaline metals are selected from the groups comprising $Na^+$ and $K^+$.

The compositions of the present invention comprise a salt of formula (I) as active ingredient, optionally in combination with one or more further active ingredients and, optionally, a pharmacologically acceptable excipient.

The aforesaid compositions comprise the enterally or parenterally administrable compositions. These generally occur as aqueous solutions generally containing 0.1–1.0 moles/liter of salt of formula (I) or a molar equivalent amount of a pharmacologically acceptable salts thereof.

In the compositions which comprise a further active ingredient, preferably this is L-carnitine or an alkanoyl L-carnitine wherein the alkanoyl group has 2–6 carbon atoms or a pharmacologically acceptable salt thereof. The composition comprises 0.1–0.5 moles/liter of L-carnitine or alkanoyl L-carnitine or a molar equivalent amount of a pharmacologically acceptable salt thereof.

What is meant by pharmacologically acceptable salt of L-carnitine or alkanoyl L-carnitine is any salt of these with an acid that does not give rise to unwanted toxic or side effect. These acids are well known to pharmacologists and to experts in pharmacy.

Non-limiting examples of such salts are: chloride; bromide; iodide; aspartate; acid aspartate; citrate; acid citrate; tartrate; phosphate; acid phosphate; fumarate; acid fumarate; glycerophosphate; glucose phosphate; lactate; maleate; acid maleate; orotate; oxalate; acid oxalate; sulphate; acid sulphate; trichloroacetate; trifluoroacetate and methanesulphonate.

A list of FDA-approved pharmacologically acceptable salts is disclosed in Int. J. Pharm. 33, (1986), 201–217; this latter publication is incorporated herein by reference.

The following non-limiting examples show the preparation of some dodecandioic salts according to the invention.

EXAMPLE 1

Preparation of L-Lysine Dodecandioate (ST 1284)

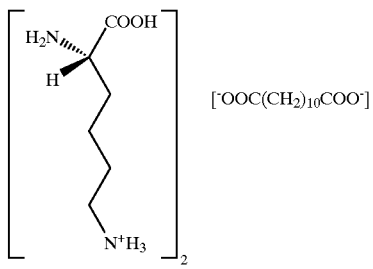

L-lysine (14.6 g; 0.1 moles) was dissolved in 250 mL of $H_2O$. Dodecandioic acid (11.5 g; 0.05 moles) was added to the resulting solution portionwise.

The resulting mixture was kept under stirring at room temperature till dissolution.

The opalescent solution thus obtained was filtered and the filtrate concentrated under vacuum to dryness at 40° C.

The residue was taken up with acetone and the resulting mixture was kept under stirring at room temperature overnight.

The mixture was then filtered and the filter cake dried under vacuum at 40° C.

25 grams of a solid, non-hygroscopic, water-soluble compound were thus obtained.

pH=7.1 (c=1% $H_2O$)

Thermal analysis: DSC=196.8° C.

NMR $D_2O$ 3.6(2H,t,2C$\underline{H}$N$H_2$); 2.9(4H,2C$\underline{H}_2$N$^+H_3$); 2.0 (4H,t,2C$\underline{H}_2$COOH); 1.7(2H,m,C$\underline{H}_2$C$H_2$COOH); 1.5(2H,m, C$H_2$C$\underline{H}_2$COOH); 1.4–1.3(6H,m,2-(C$\underline{H}_2$)$_3$N$^+H_3$; 1.1(14H, m,(C$H_2$)$_7$)

Elementary analysis for $C_{24}H_{52}N_4O_6$

|  | C % | H % | N % |
|---|---|---|---|
| Cal. (+1.9% $H_2O$) | 57.63 | 10.64 | 11.14 |
| Found | 55.30 | 10.43 | 10.59 |

HPLC analysis was conducted using two different chromatographic columns.

Column Speherisorb-SCX (5 μm) 250×4 mm

Temperature=25° C.

Eluant $CH_3CN/KH_2PO_4$ 0.1 M 50/50 pH=3.2 con $H_3PO_4$

Lysine $R_t$=18,65

Column Symmetry—C18 (5 μm) 3.9×300 mm

Temperature=30° C.

Eluant $CH_3CN/KH_2PO_4$ 0.1 M 70/30

Dodecandioic acid $R_t$=13.45

EXAMPLE 2

Preparation of L-lysine Dodecandioate, Sodium Salt (ST 1309)

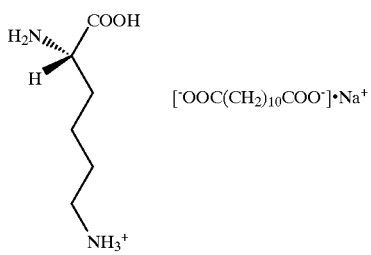

Dodecandioic acid (23 g; 0.01 moles), L-lysine (1.46 g; 0.01 moles) and $NaHCO_3$ (0.84 g; 0.01 moles) were suspended in 50 mL of $H_2O$. The resulting mixture was kept under stirring till complete dissolution. The resulting solution was brought to dryness under vacuum.

The raw residue was taken up with acetone under stirring and the mixture thus obtained was filtered.

4 g of a solid, non hygroscopic, water-soluble compound were obtained.

pH=7.5 (c=1% in $H_2O$)

Thermal analysis

The compound decomposes at about 200° C. without melting.

Elementary analysis for $C_{18}H_{35}N_2O_6Na$

|  | C | H | N |
|---|---|---|---|
| Calc. | 54.25 | 8.85 | 7.03 |
| Found | 53.63 | 9.49 | 7.25 |

NMR and HPLC as in Example 1, but in this case the molar ratio L-lysine/dodecandioic acid was 1:1.

EXAMPLE 3

Preparation of Choline Dodecandioate (ST 1313)

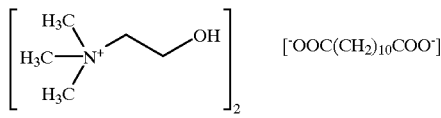

Choline chloride (1.4 g; 0.01 moles) was dissolved in water. The resulting solution was eluted on IRA-402 ($HCO_3$) resin. To the aqueous solution thus obtained dodecandioic acid (1.15 g; 0.005 moles) was added. The mixture was kept under stirring till complete dissolution (about 12 hours).

The resulting solution was concentrated under vacuum at 40° C.

2.1 g of a hygroscopic, oily compound were obtained.

EXAMPLE 4

Preparation of Choline Dodecandioate, Sodium Salt
(ST 1314)

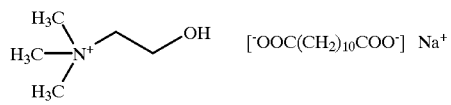   [⁻OOC(CH$_2$)$_{10}$COO⁻]  Na⁺

Dodecandioic acid (2.3 g;0.01 moles) was suspended in 50 mL of water. To the resulting suspension, first sodium bicarbonate (0.84 g; 0.01 moles) and then a 50% aqueous solution of choline (2.42 g; 0.01 moles) were added under stirring.

The mixture thus obtained was kept under stirring for 2 hours till complete dissolution, the resulting solution was concentrated under vacuum at 40° C. and the residue dried under vacuum with an oil pump.

4.9 g of a hygroscopic compound were obtained.

It is apparent that in the salts of formula (I) also the cationic moiety consisting of basic aminoacids and/or choline markedly contributes to the therapeutic/nutritional value of the salts.

Amino acids are the constituent building blocks of proteins which are metabolised in the body to produce energy.

The carbon skeletons of amino acids can be incorporated in fatty acids and in carbohydrates.

Lysine is one of the least abundant essential amino acids in nature. It is not synthesised in the human body and its supply occurs exclusively through the diet.

In mammals, the catabolism of lysine leads to the formation of acetyl coenzyme A.

Lysine is utilised as a food supplement because it favours the growth and synthesis of tissues (Feldberg Hetzel, Food Technol, 12, 496 [1958]).

Moreover, the therapeutic use of this amino acid has been proposed for the treatment and prevention of herpetic lesions (McCune et al. [1984]; Simon Van Melle and Ramelet [1985]).

Choline is a quaternary amine extensively present in food.

It is a precursor of the synthesis of the neurotranismitter acetylcholine, is a source of labile methyl groups and is a precursor of membrane phospholipids.

Choline is an essential nutrient for man. It has been demonstrated, in fact, that human cells in culture need choline for growth (Eagle H.: J. Exp. Med., 102: 595–600, 1955). Under-nourished subjects present a reduced concentration of plasma choline (Chawla R. K., Wolf D. C., Kutner M. H., Bonkovsy H. L.: Gastroenterology, 97: 15141520, 1989). Patients receiving parenteral nutrition with solutions containing low concentrations of choline develop liver dysfunctions similar to those noted in animals put on a diet deficient in choline (Sheard N. F., Tayek J. A., Bistrian B. R. et al.; Am. J. Clin Nutr., 43: 219–224, 1986).

A choline-deficient diet may also give rise to kidney abnormalities and to abnormal fertility, growth and haematopoiesis, as well as to hypertension.

Choline and phosphatidyl choline are so extensively present in food that a deficiency syndrome has been recently identified only in a hospitalized population unable to feed on normal food.

Liver abnormalities (fatty infiltrations in the liver and liver-cell damage) associated with total parenteral nutrition (TPN) have been reported by many clinical groups (Poley J. R.: In: Lebenthal E. Ed., Textbook of Gastroenterology and Nutrition in Infancy, New York, Raven Press, 1981, pp. 743–763).

TPN often has to be discontinued due to the severity of the associated liver diseases.

It has been found that subjects receiving TPN have a much lower plasma choline concentration than is found in normally fed subjects (Sheard N. F., Tayek J. A., Bistrian B. R. et al.: Am. J. Clin. Nutr., 43: 219–224, 1986).

It has been calculated that patients fed via TPN need from 1000 to 1700 µmol of choline-containing phospholipids during the first week of TPN.

After administration of choline given in the form of lecithin during TPN, it has been observed that normal plasma levels of choline are restored and that the incidence of liver dysfunctions and hepatic steatosis decreases (Buchman A. L., Dubin M., Jenden D. et al.: Gastroenterology, 102: 1363–1370, 1992).

It is clear that the salts formula (I), particularly when utilised in TPN, afford considerable benefits of both a therapeutic and nutritional nature.

What is claimed is:

1. A salt of general formula (I)

[—OOC(CH$_2$)$_{10}$COO⁻]X⁺Y⁺   (I)

wherein:
if X⁺ is the same as Y⁺, each is selected from the group consisting of the cations of lysine, arginine, hystidine, ornithine and choline; or
if X⁺ is other than Y⁺, they are selected from:
(a) the cations of lysine, arginine, hystidine, ornithine and choline; and
(b) the cations of sodium, potassium and ammonium, provided that if either of X⁺ or Y⁺ is a (b) cation, the other is an (a) cation.

2. An enterally or parenterally administratable composition comprising the salt of formula (I) of claim 1 and a pharmacologically acceptable excipient.

3. A composition according to claim 2, wherein the salt of formula (I) is di-L-lysinedodecandioate.

4. A composition according to claim 2, wherein the salt of formula (I) is the sodium salt of meno-L-lysine dodecandioate.

5. A composition according to claim 2, wherein the salt of formula (I) is a choline salt.

6. A composition according to claim 2, wherein the salt of formula (I) is di-choline dodecandioate.

7. A composition according to claim 2, wherein the salt of formula (I) is the sodium salt of monocholine dodecandioate.

8. The composition of claim 2, in the form of an aqueous solution, comprising 0.1–1 moles/liter of salt of formula (I).

9. The composition of claim 2, comprising a further active ingredient.

10. The composition of claim 9, wherein the further active ingredient is selected from the group consisting of L-carnitine and an alkanoyl L-carnitine wherein the alkanoyl group has 2–6 carbon atoms and the pharmacologically acceptable salts thereof.

11. The composition of claim 10, comprising 0.1–0.5 moles/liter of L-carnitine or alkanoyl L-carnitine or a molar equivalent amount of a pharmacologically acceptable salt thereof.

* * * * *